United States Patent
Chen et al.

(10) Patent No.: US 8,543,179 B2
(45) Date of Patent: Sep. 24, 2013

(54) BIOMEDICAL SENSOR DEVICE

(75) Inventors: Yu-Han Chen, Hsinchu (TW); Lun-De Liao, Hsinchu (TW); Paul C.-P. Chao, Hsinchu (TW); Chin-Teng Lin, Hsinchu (TW)

(73) Assignee: National Chiao Tung University, Hsinchu (TW)

( * ) Notice: Subject to any disclaimer, the term of this patent is extended or adjusted under 35 U.S.C. 154(b) by 1108 days.

(21) Appl. No.: 12/480,115

(22) Filed: Jun. 8, 2009

(65) Prior Publication Data
US 2010/0286491 A1    Nov. 11, 2010

(30) Foreign Application Priority Data
May 5, 2009  (TW) ............................... 98114844 A

(51) Int. Cl.
*A61B 5/00* (2006.01)

(52) U.S. Cl.
USPC ......................................................... 600/323

(58) Field of Classification Search
USPC ........................................................... 600/323
See application file for complete search history.

(56) References Cited

U.S. PATENT DOCUMENTS

| | | | |
|---|---|---|---|
| 2006/0195024 A1* | 8/2006 | Benni | 600/323 |
| 2008/0009763 A1* | 1/2008 | Chiou et al. | 600/544 |
| 2008/0039770 A1* | 2/2008 | Francis et al. | 604/20 |
| 2010/0210930 A1* | 8/2010 | Saylor | 600/323 |
| 2010/0261986 A1* | 10/2010 | Chin et al. | 600/324 |
| 2010/0286491 A1* | 11/2010 | Chen et al. | 600/301 |
| 2011/0004082 A1* | 1/2011 | Poeze et al. | 600/323 |

* cited by examiner

*Primary Examiner* — Rodney Fuller
(74) *Attorney, Agent, or Firm* — Muncy, Geissler, Olds & Lowe, PLLC

(57) ABSTRACT

A biomedical sensor device includes a light source, a probe array, and a photo detector. The light source is configured for emitting infrared radiation. The probe array is contacted to a user's skin to detect an electric wave signal transmitted through the probe array from the skin. The probe array includes a substrate and a plurality of probes mounted on the substrate, wherein the substrate and the probes are non-opaque so that the infrared radiation may be transmitted through the probe array into the skin. The photo detector is configured to detect an infrared signal by measuring the infrared radiation absorption by the skin.

19 Claims, 4 Drawing Sheets

BIOMEDICAL SENSOR DEVICE

BACKGROUND OF THE INVENTION

1. Field of the Invention

The present invention relates to a biomedical sensor device, and more particularly to a biomedical sensor device for measuring electric wave signal and infrared signal.

2. Description of the Prior Art

The electric wave signal measurement has been widely applied in many fields such as military, biomedicine and man-machine systems and is used for measuring EEG (electroencephalography), ECG (electrocardiography), EMG (electromyography), etc. in biomedicine field.

Conventional electric wave signal measuring instruments usually adopt wet electrodes, which require conducting gel for proper function. However, the conducting gel may cause illness to patients e.g. allergy or swelling, and can not be long-acting since the conductivity thereof would decrease in time.

Dry electrodes have been recently developed to resolve the aforementioned problems of wet electrodes. However, the signal quality for dry electrodes is quite unstable, which needs to be improved for the dry electrodes to perform optimally.

Infrared measurement has the advantages of non-invasiveness, fast and precise measurement and is thus widely adopted for measuring physiological signals, e.g. blood oxygen, blood sugar, and the like. However, the size of infrared measuring instrument is large and therefore it would highly desirable reduce the size thereof to meet the present market trend.

Though the electric wave signal measuring instrument and the infrared measuring instrument are well known to be important in medical field, however they are available two different measuring instruments. Thus, operator needs to have these instruments when measurements of electric wave signals and infrared signals are required, and therefore it is very inconvenient.

Accordingly, it is highly desirable to develop a biomedical sensor device capable of detecting electric wave signal and infrared signal for greater convenience.

SUMMARY OF THE INVENTION

The present invention is directed to provide a biomedical sensor device including an electric wave measuring device and an infrared measuring device and which functions with non-opaque probes. Thus, biomedical sensor device may be used rapidly measure an electric wave signal and infrared signal, and therefore provide greater convenience to the user.

According to one embodiment, a biomedical sensor device includes a light source, a probe array, and a photo detector. The light source is configured for emitting infrared radiation and the probe array is adopted to contact the skin of a user to measure an electric wave signal. The probe array includes a substrate and a plurality of probes mounted on the substrate, wherein the substrate and the probes are non-opaque so that the infrared radiation may be transmitted through the probe array into the skin. The photo detector is configured for detecting an infrared signal by measuring the infrared radiation absorption by the skin.

Other advantages of the present invention will become apparent from the following description taken in conjunction with the accompanying drawings wherein are set forth, by way of illustration and example, certain embodiments of the present invention.

BRIEF DESCRIPTION OF THE DRAWINGS

The foregoing aspects and many of the accompanying advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
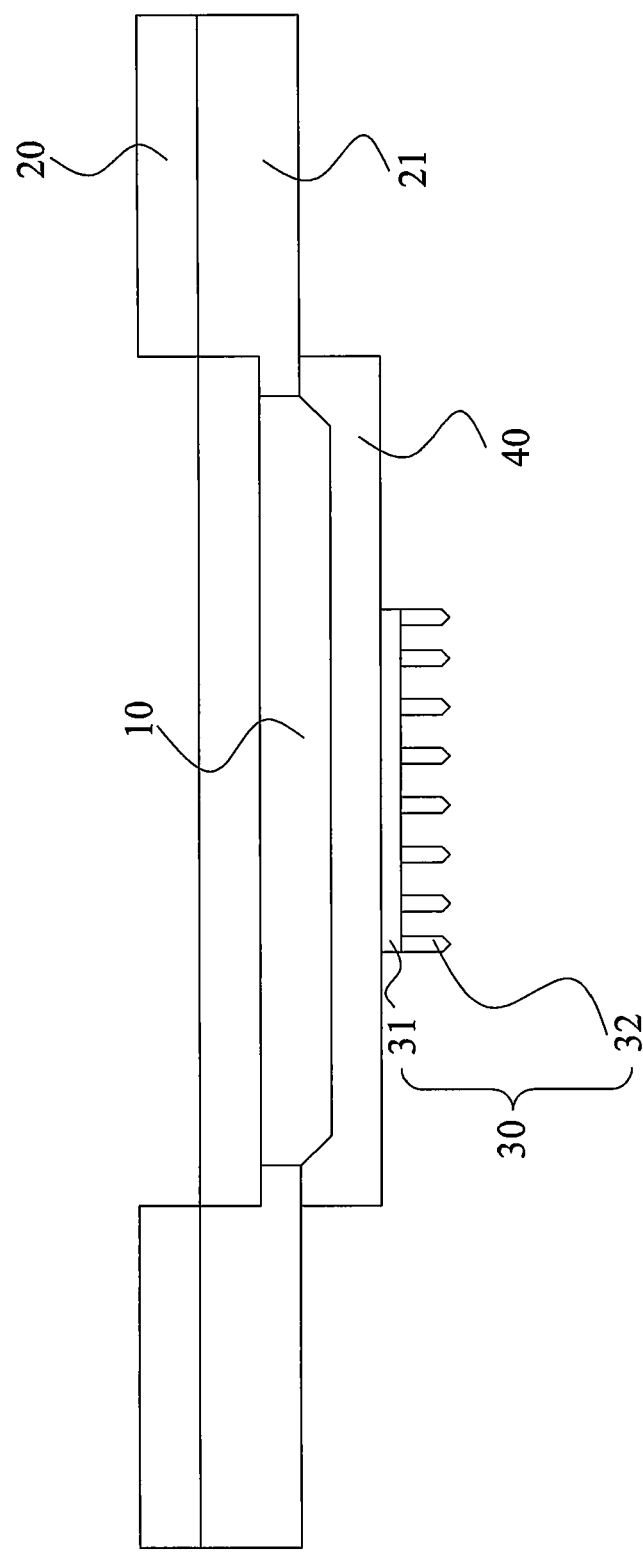
FIG. 1 is a schematic diagram illustrating a biomedical sensor device according to one embodiment of the present invention.

FIG. 1 is a schematic diagram illustrating a biomedical sensor device according to one embodiment of the present invention. The biomedical sensor device includes a light source 10, a photo detector 20, and a probe array 30. In this embodiment, the probe array 30 is connected to the light source 10 via a non-opaque adapter 40. In another embodiment, the probe array 30 may be detachably connected to the light source 10.

The biomedical sensor device may be used for measuring infrared radiation. The light source 10 comprises, for example, an infrared light-emitting diode, and is configured for emitting infrared radiation. The wavelength range of the infrared radiation is generally about 700 nm to 100 µm. In the present embodiment, the light source 10 emits near-infrared radiation whose wavelength range is about 700-1400 nm, and preferably about 700-900 nm.

Figure 2:
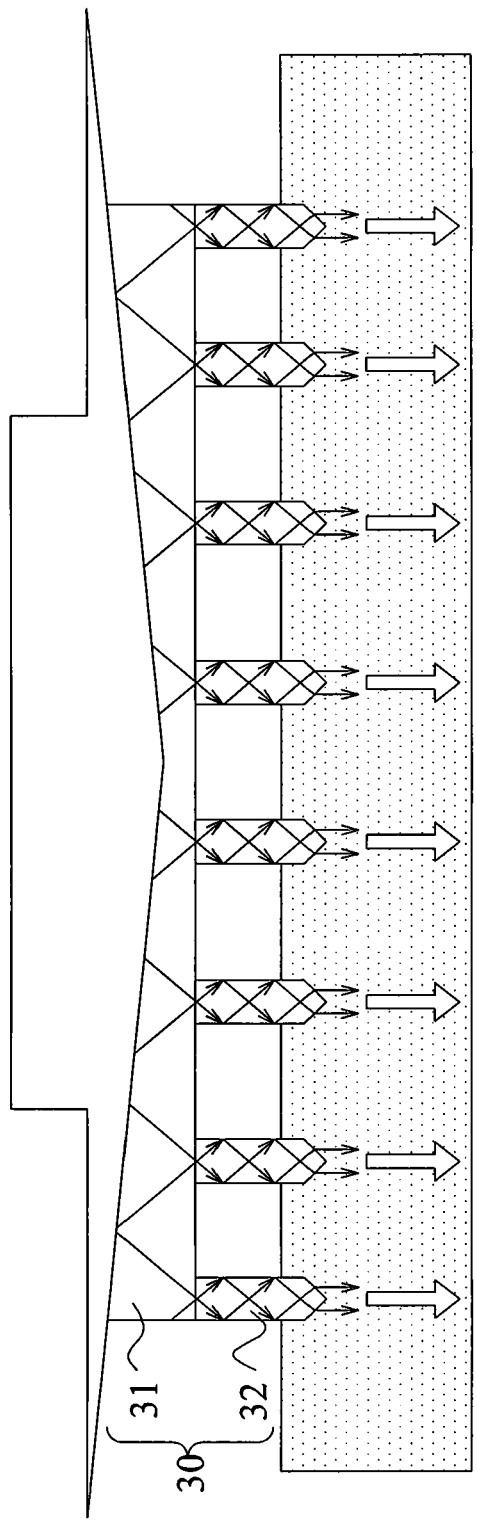
FIG. 2 is a schematic diagram illustrating transmission of infrared radiation through the probe array and contacting the skin.

FIG. 2 is a schematic diagram illustrating transmission of infrared radiation through the probe array 30 and contacting the skin. The probe array 30 includes a substrate 31 and a plurality of probes 32 mounted on the substrate 31, wherein the substrate 31 and the probes 32 are non-opaque or preferably transparent so that the infrared radiation may be transmitted there-through via reflection within the probes 32 and contact the skin when the probe array 30 is contacted to the user's skin. Referring to FIG. 1, the photo detector 20 may be configured to detect an infrared signal by measuring the infrared radiation absorption by the skin. In addition, the photo detector 20 may further include a color filter 21 for filtering out light of other wavelengths for achieving higher accuracy. For example, the infrared signal may be used but not limited for measuring the blood oxygen concentration or blood sugar concentration. For measuring blood oxygen concentration, infrared signals of two different wavelengths may be measured to analyze the ratio of oxygenated red blood cells to non-oxygenated ones.

Furthermore, the biomedical sensor device may be used for measuring an electric wave signal. The probes 32 of the probe array 30 may be contacted to the skin or preferably punctured into the skin for measuring the electric wave signal. In addition, a plurality of the biomedical sensor devices of the present invention may be placed on the skin surface to simultaneously measure a plurality of fixed-point signals, and multiple electric wave signal measurement may thus be achieved. Here, the electric wave signal may be used, but not limited, to measure EEG (electroencephalography), ECG (electrocardiography) or EMG (electromyography).

Figure 3:
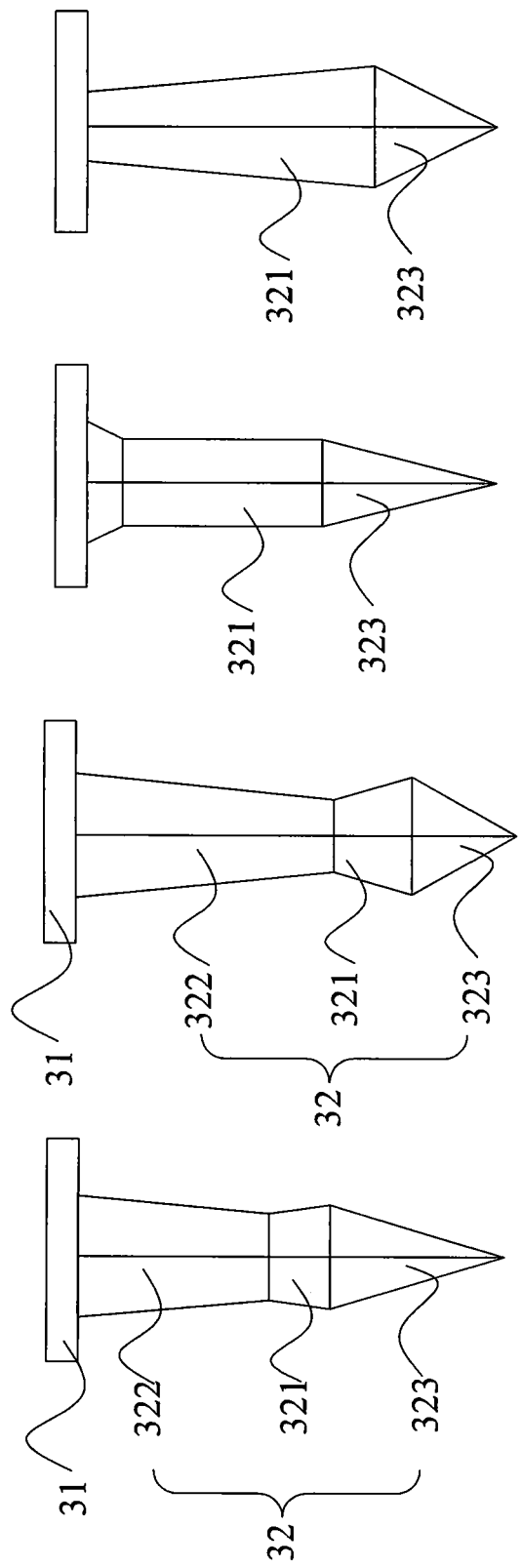
FIG. 3a-3d are schematic diagrams illustrating a structure of probes.

In addition, the probes of the present invention are improved for enhancing performance and structure stability. FIG. 3a-3d illustrate schematic diagrams of the structures of the probes. As illustrated in FIG. 3a, each of the probes 32 includes a tip portion 323, a first stalk portion 321, and a second stalk portion 322. The tip portion 323 is configured for puncturing the stratum corneum and the stratum germinativum of the user's skin to allow the probe 32 to penetrate into the stratum germinativum. The length of the tip portion 323 may be about 50-150 µm for puncturing into the stratum germinativum, for example. The length of the tip portion 323 may be about 80-100 µm. The first stalk portion 321 has its top connected to the tip portion 323, and the cross-sectional area of the top of the first stalk portion 321 is larger than that of a bottom thereof so that the first stalk portion 321 has an upward extruding conformation for increasing stability for probes 32 when puncturing the skin. The second stalk portion 322 has its bottom connected to the substrate, wherein the cross-sectional area of a top of the second stalk portion 322 is smaller than that of the bottom of the second stalk portion 322 so that the stalk portion of the probe 32 connected to the substrate has a wider shape and is more sturdy.

FIG. 3b illustrates a probe structure similar to that illustrated in FIG. 3a, wherein the tip portion 323, the first stalk portion 321 and the second stalk portion 322 are designed for achieving the same purpose. However, the probe structure of the present invention is not limited thereto. For example, each of the probes illustrated in FIGS. 3c and 3d includes only a tip portion 323 and a first stalk portion 321. It is also understood that the probe structure of the present invention may include, without limitation, to the structures illustrated in FIGS. 3c and 3d.

In addition, compared to those illustrated in FIGS. 3c and 3d, the probe structure illustrated in FIG. 3a has better output performance of signals at different depth profile (data not shown) in tests of electrode performance processed by electromagnetic simulation. Therefore, the probes of the present invention are designed with electric field optimization and enjoy the advantages of sturdiness, more puncturing stability and better performance.

The manufacturing process for the above-mentioned probes includes without limitation to (a) micro electro mechanical systems (MEMS), (b) LIGA process and (c) injection molding process.

In one embodiment of the present invention, the substrate may be made of well known materials applied in MEMS including without limitation to silicon, silicon dioxide or zinc oxide. The probes may be made of TCO (transparent conducting oxides) including without limitation to ITO (tin doped Indium oxide), FTO (fluorine doped tin dioxide), AZO (aluminum doped zinc oxide) or GZO (gallium doped zinc oxide).

In another embodiment of the present invention, the probe further includes a conductive layer covering the tip portion and the first stalk portion. Here, the tip portion and first stalk portion may be made of well known materials applied in MEMS including without limitation to silicon, silicon dioxide or zinc oxide. The conductive layer may be made of polymer, thin film material or metal.

Furthermore, an optimal distance between the light source and the photo detector may be maintained since the infrared radiation may be reflected by the skull if the distance is too short distance and over-absorbed if the distance is too long.

Figure 4:
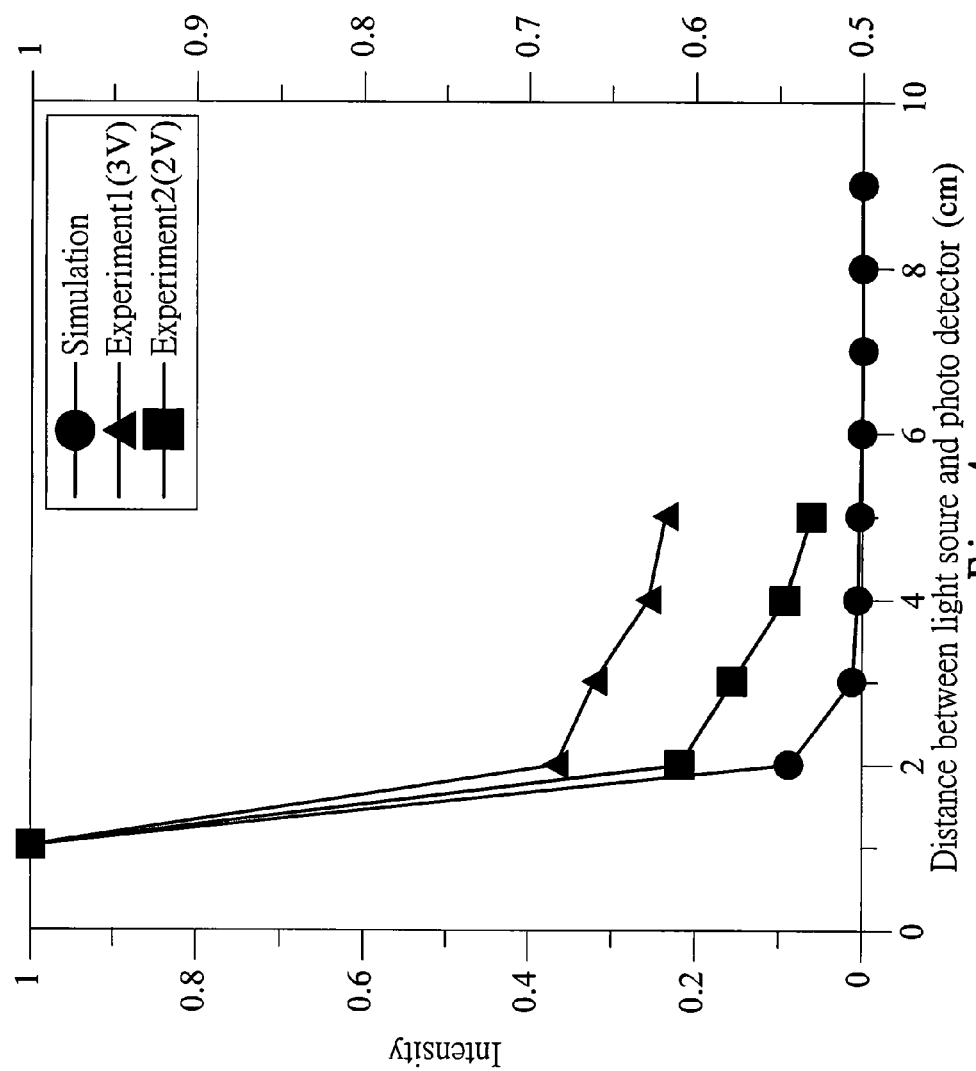
FIG. 4 is a diagram illustrating a distance between the light source and a photo detector.

As illustrated in FIG. 4, the optimal distance between the light source and the photo detector is in a range of about 2-4 cm, which is obtained via simulation experimentation.

The biomedical sensor device of the present invention may be applied in treatment of cerebral injury, for example. Sustained cerebral lesion caused by the damaged cerebral nerve cells or tissues occurs frequently in cerebral injury. For now, the changes in HEG (hemoencephalography) have been found to correlate with the damage level and the HEG measurement may assist the diagnosis of patient conducted by medical professionals. However, presently EEG and HEG measurement can not be performed with the same instrument, and therefore the pathological diagnosis of cerebral injury may be more time-consuming and the emergency medical treatment cannot be timely performed. The biomedical sensor device of the present invention has the capability to perform both EEG and HEG measurements so that both EEG and HEG measurements may be rapidly performed, individually or simultaneously, to timely diagnose and provide appropriate and prompt medical treatment to the patient.

An embodiment of the present invention provides a biomedical sensor device capable of measuring EEG and HEG. A plurality of the biomedical sensor devices as illustrated in FIG. 1 may be placed on the skin surface to measure a plurality of fixed-point signals. For measuring EEG signals, the probes 32 may puncture into Stratum Germinativum to obtain EEG signals. The near-infrared radiation emitted by the light source 10 shows differential absorption and reflection level for different cerebral blood oxygen level and is detected as a near-infrared signal by the photo detector 20 for measuring HEG. The EEG and HEG signals are then output to and processed by the back-end electronics and are then further output and displayed on man-machine interface.

To sum up, the biomedical sensor device provided by the present invention comprises both an electric wave measuring device and an infrared measuring device and capable of rapidly measuring both EEG and HEG using non-opaque probes. The non-opaque probes are contacted to a user's skin to detect an electric wave signal and configured as a transmitting medium for precisely measuring infrared radiation so that the infrared radiation measurement can be effectively improved.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A biomedical sensor device, comprising:
a light source, configured for emitting infrared radiation;
a probe array, for contacting to a user's skin and for detecting an electric wave signal from the skin, and comprising a substrate and a plurality of probes mounted on the substrate, wherein the substrate and the probes are non-opaque whereby the infrared radiation transmits through the probe array into the skin, wherein each of the probes comprises:
a tip portion;
a first stalk portion, comprising a top thereof connected to the tip portion, wherein a cross-sectional area of the top is larger than that of a bottom of the first stalk portion; and
a second stalk portion comprising a bottom thereof connected to the substrate, and wherein the cross-sectional area of a top of the second stalk portion is smaller than that of the bottom of the second stalk portion; and a photo detector, configured for detecting an infrared signal by measuring the infrared radiation absorption by the skin.

2. The biomedical sensor device as claimed in claim 1, wherein the photo detector further comprises a color filter.

3. The biomedical sensor device as claimed in claim 1, wherein the infrared signal is used for measuring blood oxygen concentration or blood sugar concentration.

4. The biomedical sensor device as claimed in claim 1, wherein the electric wave signal is used for measuring EEG (electroencephalography), ECG (electrocardiography) or EMG (electromyography).

5. The biomedical sensor device as claimed in claim 1, wherein the substrate and the probes are transparent.

6. The biomedical sensor device as claimed in claim 1, wherein the substrate is made of silicon, silicon dioxide or zinc oxide.

7. The biomedical sensor device as claimed in claim 1, wherein the probes are made of TCO (transparent conductive oxides).

8. The biomedical sensor device as claimed in claim 7, wherein the TCO comprises ITO (tin doped Indium oxide), FTO (fluorine doped tin dioxide), AZO (aluminum doped zinc oxide) or GZO (gallium doped zinc oxide).

9. The biomedical sensor device as claimed in claim 1, wherein the tip portion and the first stalk portion are made of silicon, silicon dioxide or zinc oxide.

10. The biomedical sensor device as claimed in claim 1, wherein each of the probes further comprises a conductive layer covering the tip portion and the first stalk portion.

11. The biomedical sensor device as claimed in claim 10, wherein the conductive layer is made of a polymer, a thin film material or a metal.

12. The biomedical sensor device as claimed in claim 1, wherein the tip portion is configured for puncturing stratum corneum and the stratum germinativum of the skin to allow the probe to penetrate into the stratum germinativum.

13. The biomedical sensor device as claimed in claim 1, wherein a length of the tip portion is about 50-150 μm.

14. The biomedical sensor device as claimed in claim 1, wherein the length of the tip portion is about 80-100 μm.

15. The biomedical sensor device as claimed in claim 1, wherein the light source comprises an infrared light-emitting diode.

16. The biomedical sensor device as claimed in claim 1, wherein a distance between the light source and the photo detector is about 2-4 cm.

17. The biomedical sensor device as claimed in claim 1, wherein a wavelength range of the infrared is between 700 nm to 100 μm.

18. The biomedical sensor device as claimed in claim 1, wherein a wavelength range of the infrared is between 700-1400 nm.

19. The biomedical sensor device as claimed in claim 1, wherein a wavelength range of the infrared is between 700-900 nm.

* * * * *